United States Patent
Huang

(10) Patent No.: US 8,797,443 B2
(45) Date of Patent: Aug. 5, 2014

(54) METHOD FOR CHECKING CAMERA

(75) Inventor: Wen-Lung Huang, New Taipei (TW)

(73) Assignee: Wistron Corporation, New Taipei (TW)

( * ) Notice: Subject to any disclaimer, the term of this patent is extended or adjusted under 35 U.S.C. 154(b) by 44 days.

(21) Appl. No.: 13/592,991

(22) Filed: Aug. 23, 2012

(65) Prior Publication Data
US 2013/0250127 A1 Sep. 26, 2013

(30) Foreign Application Priority Data
Mar. 26, 2012 (TW) .............................. 101110392 A

(51) Int. Cl.
H04N 5/222 (2006.01)
H04N 5/202 (2006.01)
H04N 5/232 (2006.01)
H04N 5/238 (2006.01)
H04N 5/217 (2011.01)

(52) U.S. Cl.
USPC ...... 348/333.04; 348/254; 348/345; 348/363; 348/241

(58) Field of Classification Search
CPC .................................. H04N 5/23293
USPC .......... 348/254, 671, E9.054, E5.074, 207.1, 348/241, 247, 252, 245, 187, 333.04, 363, 348/345; 382/162, 163, 165, 169
See application file for complete search history.

(56) References Cited

U.S. PATENT DOCUMENTS

| | | | |
|---|---|---|---|
| 5,982,943 A * | 11/1999 | Hsu et al. ...................... | 382/270 |
| 7,027,662 B2 * | 4/2006 | Baron ........................... | 382/275 |
| 2004/0062438 A1 * | 4/2004 | Jia ................................ | 382/169 |
| 2004/0118919 A1 * | 6/2004 | Breytman et al. ............. | 235/454 |
| 2009/0135455 A1 * | 5/2009 | Li ................................. | 358/487 |
| 2012/0206613 A1 * | 8/2012 | Yoshida ..................... | 348/207.1 |

* cited by examiner

Primary Examiner — Nhan T Tran
Assistant Examiner — Chan Nguyen
(74) Attorney, Agent, or Firm — GableGotwals

(57) ABSTRACT

A method for checking a camera includes the steps of capturing an image of an object using a photo-sensitive element, converting the color level value of each of a plurality of pixels of the image into image gray level values, and when one of the image gray level values is higher than a predetermined gray level threshold value, displaying an alarm message on the screen of the camera. A camera is also disclosed herein.

7 Claims, 4 Drawing Sheets

METHOD FOR CHECKING CAMERA

RELATED APPLICATIONS

This application claims priority to Taiwan Application Serial Number 101110392, filed Mar. 26, 2012, which is herein incorporated by reference.

BACKGROUND

1. Technical Field Disclosure

The embodiment of the present disclosure relates generally to a checking method and, more particularly, to a method for checking a camera and to a camera applying the method.

2. Description of Related Art

With the prevalence of digital single lens reflex cameras (DSLRs) in is recent years, many optical manufacturers are producing a variety of lenses according to different requirements, such that users are able to adopt different kinds of lenses and thereby enjoy the benefit of capturing pictures with different focal lengths. However, the problem of dust entering the camera is increased with the changing of the lenses.

To remove the dust accumulated during changing of the lenses, there is a need to perform complex camera set-up processes manually in order to check for the presence of dust on a sensor of the camera. Such camera set-up processes are extremely complex, particularly for ordinary users.

In summary, the existing apparatus and techniques still have obvious defects and need further improvement. In order to solve the above problems, those skilled in the art are trying hard to find a solution, but no suitable method has been proposed.

SUMMARY

A method for checking a camera and a camera applying the method are provided. The method and camera address the problem of having to perform complex camera set-up processes manually when using a conventional camera in order to check for the presence of dust on a sensor of the camera.

Thus, one aspect of the embodiment of the present disclosure is to provide a method for checking a camera. The method for checking a camera comprises is the steps of capturing an image of an object using a photo-sensitive element, converting a color level value of each of a plurality of pixels of the image into an image gray level value, and displaying an alarm message on a screen of the camera when one of the image gray level values is higher than a predetermined gray level threshold value.

In another aspect of the embodiment of the present disclosure, a method for checking a camera is provided. The method for checking a camera comprises the steps of capturing an image of an object using a photo-sensitive element, acquiring a green level value of each of a plurality of pixels of the image, and displaying an alarm message on a screen of the camera when one of the green level values is higher than a predetermined green level threshold value.

In yet another aspect of the embodiment of the present disclosure, a camera is provided. The camera comprises a photo-sensitive element and a controller. The controller is electrically connected to the photo-sensitive element. The photo-sensitive element is operable to capture an image of an object. The controller is operable to convert a color level value of each of a plurality of pixels of the image into an image gray level value, and the controller is operable to generate an alarm message to display on a screen of the camera when one of the image gray level values is higher than a predetermined gray level threshold value.

In still another aspect of the embodiment of the present disclosure, a camera is provided. The camera comprises a photo-sensitive element and a controller. The controller is electrically connected to the photo-sensitive element. The photo-sensitive element is operable to capture an image of an object. The controller is operable to acquire a green level value of each of a plurality of pixels of the image, and the controller is operable to generate an alarm message to display on a screen of the camera when one of the green level values is greater than a predetermined green level threshold value.

In summary, the embodiments of the present disclosure provide a method for checking a camera and a camera applying the method. The method and camera address the problem of having to perform complex camera set-up processes manually when using a conventional camera in order to check for the presence of dust on a sensor of the camera. Moreover, the method and the camera of the embodiments of the present disclosure enable accurate checking for the presence of dust on the sensor.

BRIEF DESCRIPTION OF THE DRAWINGS

The disclosure can be more fully understood by reading the following detailed description of the embodiments, with reference made to the accompanying drawings as follows.

DETAILED DESCRIPTION

Figure 1:
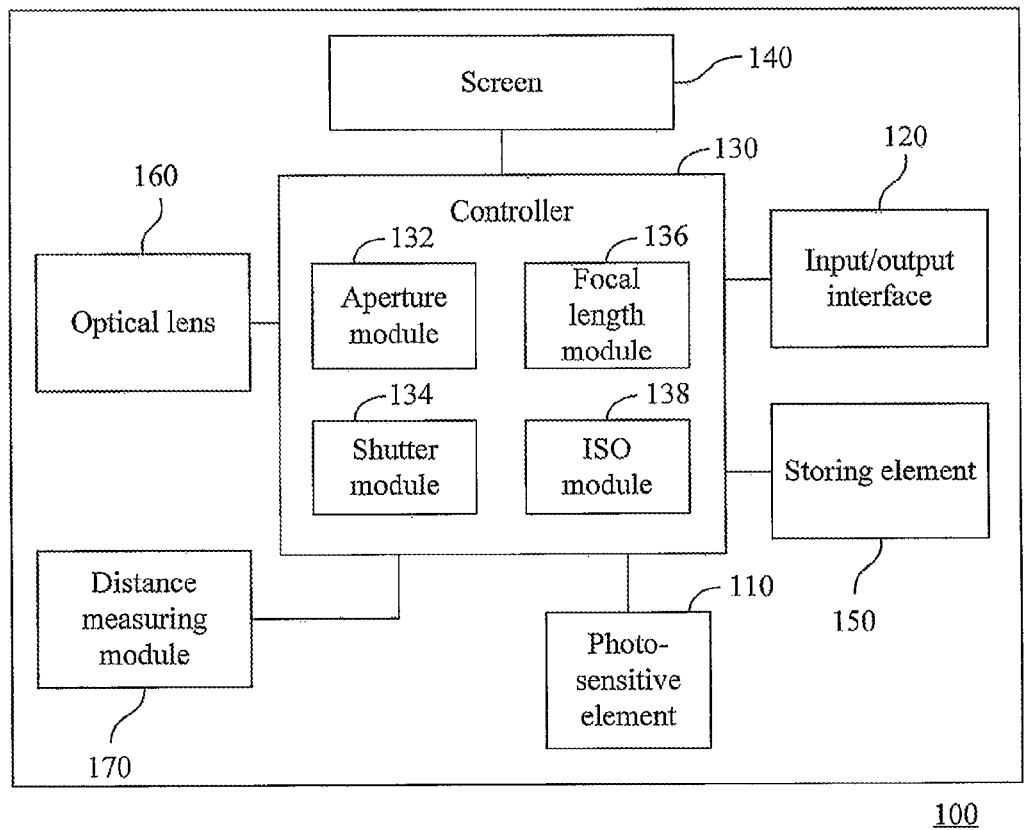
FIG. 1 schematically shows a circuit block diagram of a camera according to embodiments of the present disclosure.

The present disclosure is more particularly described in the following examples that are intended as illustrative only since numerous modifications and variations therein will be apparent to those skilled in the art. Various embodiments of the disclosure are now described in detail. Referring to the drawings, like numbers indicate like components throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. The use of examples anywhere in this specification, including examples of any terms discussed herein, is illustrative only, and in no way limits the scope and meaning of the disclosure or of any exemplified term. Likewise, the disclosure is not limited to various embodiments given in this specification.

As used herein, "around," "about" or "approximately" shall generally mean within 20 percent, preferably within 10 percent, and more preferably within 5 percent of a given value or range. Numerical quantities given herein are approximate, meaning that the term "around," "about" or "approximately" can be inferred if not expressly stated.

As used herein, the terms "comprising," "including," "having," "containing," "involving," and the like are to be understood to be open-ended, i.e., to mean including but not limited to.

FIG. 1 schematically shows a circuit block diagram of a camera 100 according to embodiments of the present disclosure. As shown in the figure, in one aspect of the present disclosure, the camera 100 includes a photo-sensitive element 110, an input/output interface 120, a controller 130, a screen 140, a storing element 150, an optical lens 160, and a distance measuring module 170. Furthermore, the controller 130 includes an aperture module 132, a shutter module 134, a focal length module 136, and an ISO module 138.

With respect to configuration, the photo-sensitive element 110, the input/output interface 120, the screen 140, the storing element 150, the optical lens 160, and the distance measuring module 170 are all electrically connected to the controller 130.

The problem of lost focus generated by capturing an image with the same color scheme (for example, white) can be solved through use of the distance measuring module 170 of the embodiment of the present disclosure to measure the distance between an object and the camera. Subsequently, the controller 130 is operable to control the optical lens 160 to perform a focusing process according to the distance, thereby solving the problem of lost focus.

In addition, the input/output interface 120 is operable to set the aperture value and the shutter value of the optical lens 160 respectively through the aperture module 132 and the shutter module 134 of the controller 130 such that the photo-sensitive element 110 is operable to capture the image of an object through the optical lens 160 according to the distance. In another embodiment of the present disclosure, the aperture module 132 of the controller 130 is operable to set the aperture value of the optical lens 160 by obtaining a predetermined aperture value from the storing element 150, and the shutter is module 134 of the controller 130 is operable to set the shutter value of the optical lens 160 by obtaining a predetermined shutter value from the storing element 150, such that the photo-sensitive element 110 is operable to capture the image of the object through the optical lens 160 according to the distance. Hence, the camera 100 is operable to obtain a predetermined parameter value from the storing element 150 to adjust the optical lens 160 automatically so as to address the problem of having to perform complex camera set-up processes manually when using a conventional camera in order to check for the presence of dust on a sensor of the camera.

Moreover, the controller 130 is operable to convert the color level value of each of the pixels of the image into an image gray level value, and the controller 130 is also operable to determine whether one of the image gray level values is greater than a predetermined gray level threshold value. When one of the gray level values is greater than the predetermined gray level threshold value, the controller 130 is operable to generate an alarm message, and the screen 140 of the camera 100 is operable to display the alarm message.

In one embodiment, the input/output interface 120 is operable to adjust the predetermined gray level threshold value. In addition, the input/output interface 120 is further operable to set the aperture value and adjust the predetermined gray level threshold value according to the aperture value.

For example, it can be determined that there is dust on the photo-sensitive is element 110 if one of the image gray level values is greater than the predetermined gray level threshold value. When this occurs, in order to warn a user to perform a clear process, an alarm message will be displayed on the screen 140 of the camera 100. In addition, the gray level threshold value is adjusted according to aperture value due to the fact that there are different standards related to the problem of dust when adopting different apertures. Hence, the embodiment of the present disclosure can adaptively adjust standards related to the problem of dust according to different apertures such that the operation of the camera 100 of the embodiment of the present disclosure is more convenient.

In one embodiment, the controller 130 is further operable to detect a position of a pixel with an image gray level value that is greater than the predetermined gray level threshold value, and to display information of the position on the screen 140 of the camera 100.

Figure 2:
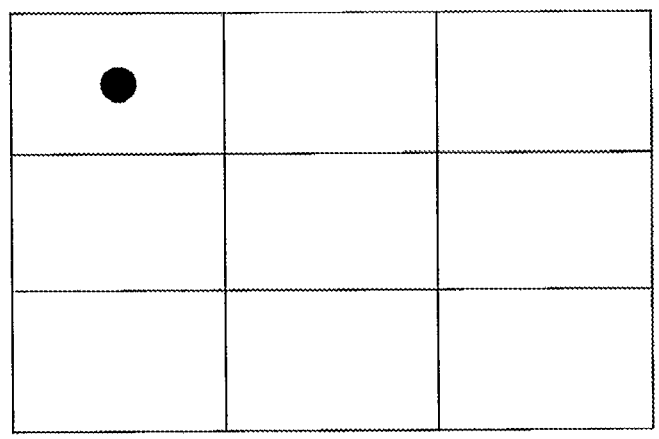
FIG. 2 schematically shows a diagram of a display frame of a camera screen according to embodiments of the present disclosure.

An example will now be provided with reference to FIG. 2 which schematically shows a diagram of a display frame of a camera screen according to embodiments of the present disclosure. In this exemplary embodiment, a division into nine squares is used. When the controller 130 detects that a position of a pixel with an image gray level value that is greater than the predetermined gray level threshold value is located on the upper left corner, the controller 130 will output a position signal according to the position. Subsequently, information of the position is displayed on the screen of the camera 100 as shown in FIG. 2. Hence, a user can perform a dust-disposal process only with respect to the area of the photo-sensitive element 110 on which the dust is present such that the risk of contaminating the photo-sensitive element 110 can be reduced.

Compared with the previous aspect of the present disclosure, in another embodiment, the main difference is the operation mode of the camera 100. First of all, in order to prevent the problem of lost focus, the embodiment of the present disclosure can employ the distance measuring module 170 to measure the distance between an object and the camera 100. The controller 130 is then operable to control the optical lens 160 to perform a focusing process according to the distance.

In addition, the input/output interface 120 is operable to set the aperture value and the shutter value of the optical lens 160 respectively through the aperture module 132 and the shutter module 134 of the controller 130 such that the photo-sensitive element 110 is operable to capture the image of the object through the optical lens 160 according to the distance. In another embodiment of the present disclosure, the aperture module 132 of the controller 130 is operable to set the aperture value of the optical lens 160 by obtaining a predetermined aperture value from the storing element 150, and the shutter module 134 of the controller 130 is ° operable to set the shutter value of the optical lens 160 by obtaining a predetermined shutter value from the storing element 150, such that the photo-sensitive element 110 is operable to capture the image of the object through the optical lens 160 according to the distance. Hence, the camera 100 is operable to obtain a predetermined parameter value from the storing element 150 to adjust the optical lens 160 automatically so as to address the problem of having to perform complex camera set-up processes manually when using a conventional camera in order to check for the presence of dust on a sensor of the camera.

Moreover, the controller 130 is operable to acquire the green level value of each of the pixels of the image, and the controller 130 is also operable to determine whether one of the green level values is greater than a predetermined green level threshold value. When one of the green level values is greater than the predetermined green level threshold value, the controller 130 is operable to generate an alarm message, and the screen 140 of the camera 100 is operable to display the alarm message.

In one embodiment, the input/output interface 120 is operable to adjust the predetermined green level threshold value. In addition, the input/output interface 120 is further operable to set the aperture value and adjust the predetermined green level threshold value according to the aperture value.

For example, it can be determined that there is dust on the photo-sensitive element 110 if one of the green level values is greater than the predetermined green level threshold value. When this occurs, in order to warn a user to perform a clear process, an alarm message will be displayed on the screen 140 of the camera 100. In addition, the green level threshold value is adjusted according to aperture value due to the fact that there are different standards related to the problem of dust when adopting different apertures. Hence, the embodiment of the present disclosure can adaptively adjust standards related to the problem of dust according to different apertures such that the operation of the camera 100 of the embodiment of the present disclosure is more convenient.

In one embodiment, controller 130 is further operable to detect a position of a pixel with a green level value that is greater than the predetermined green level threshold value, and to display information of the position on the screen of the camera. An example will now be provided with reference to FIG. 2 which schematically shows a diagram of a display frame of a camera screen according to embodiments of the present disclosure. In this exemplary embodiment, a division into nine squares is used. When controller 130 detects that a position of a pixel with a green level value that is greater than the predetermined green level threshold value is located on the upper left corner, the controller 130 will output a corresponding position signal according to the position. Subsequently, information of the position is displayed on the screen of the camera 100 as shown in FIG. 2. Hence, a user can perform a dust-disposal process only with respect to the area of the photo-sensitive element 110 on which the dust is present such that the risk of contaminating the photo-sensitive element 110 can be reduced.

In still another embodiment, the controller 130 is further operable to acquire a red level value, the green level value, and a blue level value of each of the pixels of the image, and the controller 130 is operable to generate the alarm message to display on the screen 140 of the camera 100 when one of the red, green, and blue level values is greater than a corresponding predetermined red level threshold value, the corresponding predetermined green level threshold value, or a corresponding predetermined blue level threshold value.

Figure 3:
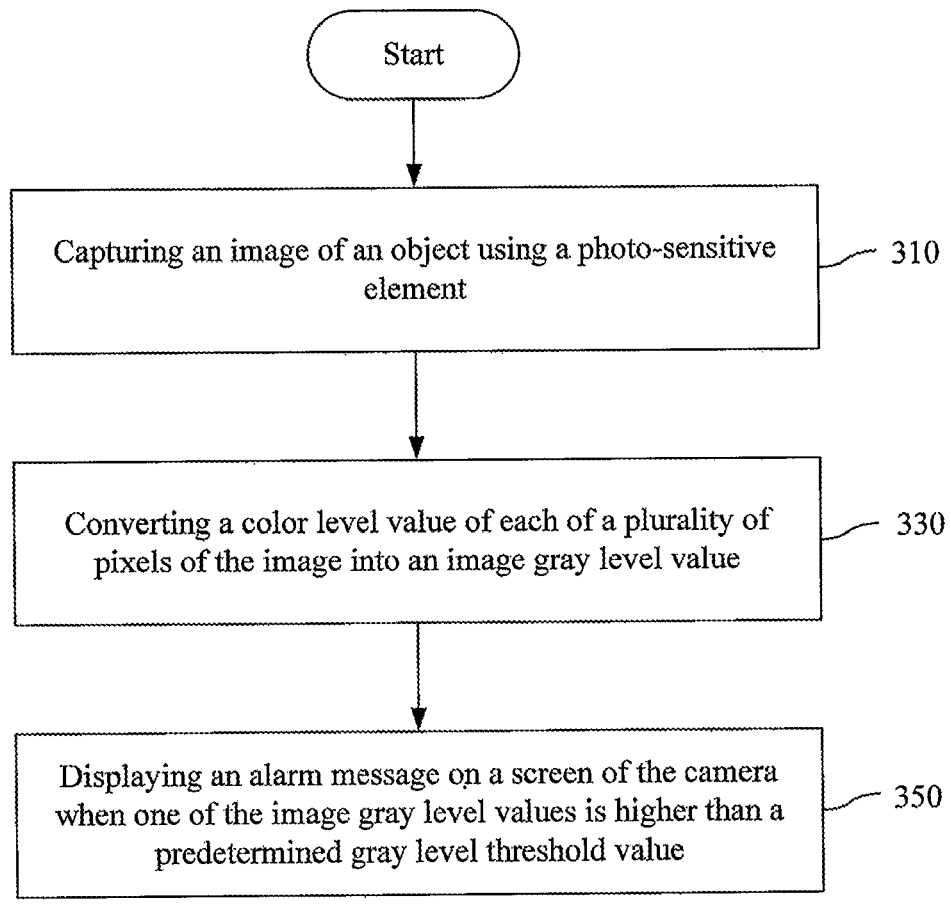
FIG. 3 schematically shows a flow diagram of a method for checking a camera according to embodiments of the present disclosure.

FIG. 3 schematically shows a flow diagram of a method 300 for checking a camera according to embodiments of the present disclosure. As shown in the figure, the method for checking a camera 300 comprises the steps of capturing an image of an object using a photo-sensitive element (step 310), converting the color level value of each of the pixels of the image into an image gray level value (step 330), and displaying an alarm message on the screen of the camera when one of the image gray level values is higher than a predetermined gray level threshold value (step 350). Hence, it can be determined that there is dust on a photo-sensitive element 110 if one of the image gray level values is greater than the predetermined gray level threshold value. When this occurs, in order to warn a user to perform a clear process, an alarm message will be displayed on the screen 140 of the camera 100.

Figure 4:
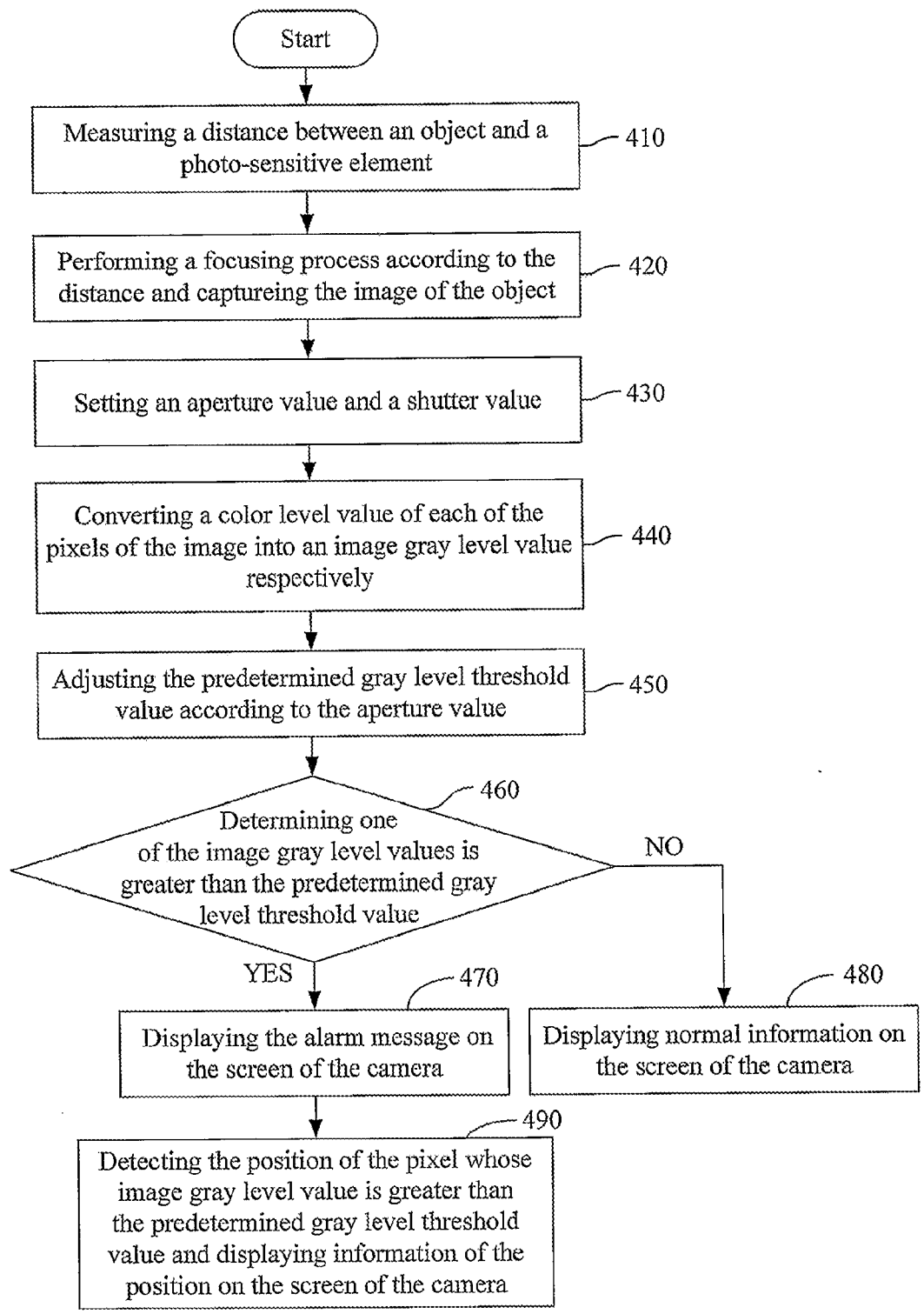
FIG. 4 schematically shows a flow diagram of a method for checking a camera according to embodiments of the present disclosure.

FIG. 4 schematically shows a flow diagram of a method 400 for checking a camera according to embodiments of the present disclosure.

Reference is now made to both FIG. 1 and FIG. 4. In step 410, a distance between an object and a photo-sensitive element is measured by the is distance measuring module 170. In step 420, a focusing process is performed by the focal length module 136 of the controller 130 according to the distance and the image of the object is captured using the photo-sensitive element 110. In step 430, an aperture value and a shutter value are set by the aperture module 132 and the shutter module 134 of the controller 130 respectively. In another embodiment of the present disclosure, the aperture value and the shutter value of the optical lens 160 are set by obtaining a predetermined aperture value and a predetermined shutter value from the storing element 150 by the aperture module 132 and the shutter module 134 of the controller 130. In step 440, a color level value of each of the pixels of the image is converted into an image gray level value. In step 450, the predetermined gray level threshold value is adjusted according to the aperture value. In step 460, a determination is made as to whether one of the image gray level values is greater than the predetermined gray level threshold value, and in step 470, the alarm message is displayed on the screen of the camera if one of the image gray level values is greater than the predetermined gray level threshold value. On the other hand, in step 480, normal information is displayed on the screen of the camera if the image gray level values are all not greater than the predetermined gray level threshold value. After step 470, a position of a pixel with an image gray level value that is greater than the predetermined gray level threshold value is detected, and information of the position is displayed on the screen of the camera in step 490. Hence, a user can perform a dust-disposal process only with respect to the area of the photo-sensitive element 110 on which the dust is present such that the risk of contaminating the photo-sensitive element 110 can be reduced.

For example, it can be determined that there is dust on the photo-sensitive element 110 if one of the image gray level values is greater than the predetermined gray level threshold value. When this occurs, in order to warn a user to perform a clear process, an alarm message will be displayed on the screen 140 of the camera 100. In addition, the gray level threshold value is adjusted according to aperture value due to the fact that there are different standards related to the problem of dust when adopting different apertures. Hence, the embodiment of the present disclosure can adaptively adjust standards related to the problem of dust according to different apertures such that the operation of the camera 100 is more convenient when the camera 100 employs the method 400 for checking the camera 100 of the embodiment of the present disclosure.

Compared with the method 300 for checking a camera as shown if FIG. 3, the method 400 for checking a camera described with reference to FIG. 4 further comprises step 410 and step 420. Referring to both FIG. 1 and FIG. 4, the method 400 for checking a camera of the embodiment of FIG. 4 can solve the problem of lost focus generated by capturing an image with the same color scheme (for example, white) through the step of measuring the distance between the object and the camera by the distance measuring module 170 and performing the focusing process according to the distance in step 420. The image of the object can be captured through the optical lens 160 of the photo-sensitive element 110.

Figure 5:
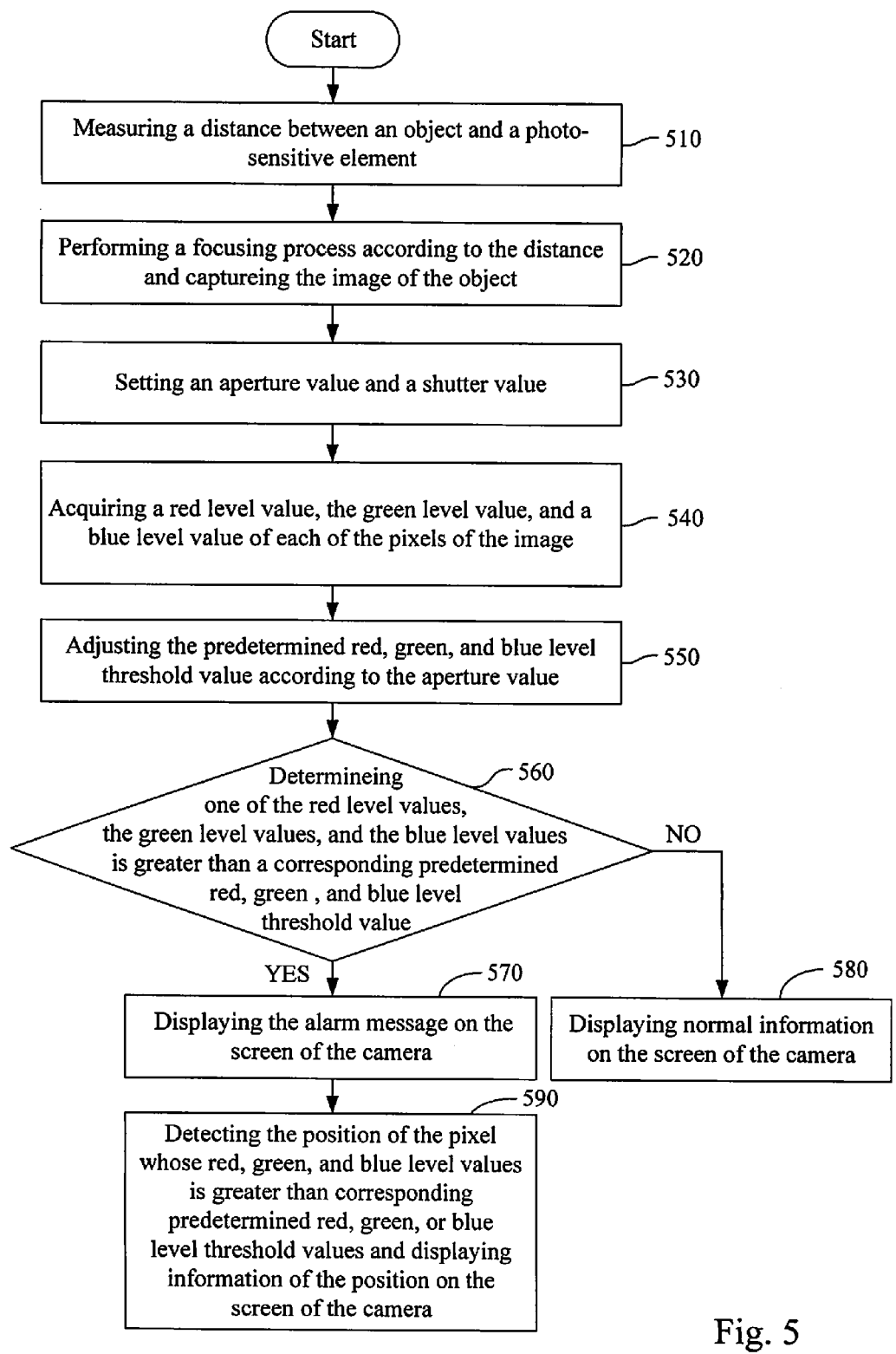
FIG. 5 schematically shows a flow diagram of a method for checking a camera according to embodiments of the present disclosure.

FIG. 5 schematically shows a flow diagram of a method 500 for checking a camera according to embodiments of the present disclosure. Reference is now made to both FIG. 1 and FIG. 5. Due to the fact that the lost focus problem frequently occurs when capturing an image with the same color scheme (for example, white), the distance between an object and the camera can be measured by the distance measuring module 170 in step 510 of the embodiment of the present disclosure, and the focusing process can be performed according to the distance in step 520 to solve the problem of lost focus. The image of the object can be captured through the optical lens 160 of the photo-sensitive element 110.

Referring to step 530, an aperture value and a shutter value of the optical lens 160 are set by the aperture module 132 and the shutter module 134 of the controller 130 respectively. In another embodiment of the present disclosure, the aperture value and the shutter value of the optical lens 160 are set by obtaining a predetermined aperture value and a predetermined shutter value from the storing element 150 by the aperture module 132 and the shutter module 134 of the controller 130. Hence, the method 500 for checking a camera of the embodiment of the present disclosure is performed to obtain a predetermined parameter value from the storing element 150 to adjust the optical lens 160 automatically so as to address the problem of having to perform complex camera set-up processes manually when using a conventional camera in order to check for the presence of dust on a sensor of the camera.

In step 540, a red level value, a green level value, and a blue level value of each of the pixels of the image can be acquired by the controller 130.

In step 550, a predetermined red level threshold value, a predetermined green level threshold value, and a predetermined blue level threshold value can be adjusted according to the aperture by the input/output interface 120. In step 560, a determination is made by the controller 130 as to whether one of the red level values, the green level values, and the blue level values is greater than a corresponding predetermined red level threshold value, a corresponding predetermined green level threshold value, or a corresponding predetermined blue level threshold value. In addition, the predetermined red level threshold value, the predetermined green level threshold value, and the predetermined blue level threshold value can be adjusted according to the aperture value due to the fact that there are different standards related to the problem of dust when adopting different apertures. Hence, the embodiment of the present disclosure can adaptively adjust standards related to the problem of dust according to different apertures such that the operation of the camera 100 is more convenient when the camera 100 employs the method 500 for checking the camera 100 of the embodiment of the present disclosure.

As mentioned above, if one of the color level values is greater than the corresponding color level threshold value, the alarm message is displayed on the screen of the camera in step 570. If all of the color level values are less than or equal to the corresponding color level threshold values, normal information is displayed on the screen of the camera in step 580.

For example, it can be determined that there is dust on a photo-sensitive element 110 if one of the color level values is greater than the corresponding color level threshold value. When this occurs, in order to warn a user to perform a clear process, an alarm message will be displayed on the screen 140 of the camera 100.

In step 590, detection is performed with respect to a position of a pixel with one of a red level value, a green level value, and a blue level value that is greater than the corresponding predetermined red level threshold value, the corresponding predetermined green level threshold value, or the corresponding predetermined blue level threshold value, and information of the position is displayed on the screen of the camera. Hence, a user can perform a dust-disposal process only with respect to the area of the photo-sensitive element 110 on which the dust is present such that the risk of contaminating the photo-sensitive element 110 can be reduced.

Those having skill in the art will appreciate that the method 300, 400, 500 for checking a camera can be performed with software, hardware, and/or firmware. For example, if an implementer determines that speed and accuracy are paramount, the implementer may opt for a mainly hardware and/or firmware implementation; alternatively, if flexibility is paramount, the implementer may opt for a mainly software implementation; or, yet again alternatively, the implementer may opt for some combination of hardware, software, and/or firmware. Those skilled in the art will recognize that optical aspects of implementations will typically employ optically oriented hardware, software, and or firmware.

In addition, those skilled in the art will appreciate that each of the steps of the method 300, 400, 500 for checking a camera is named in accordance with the function performed in said step, and such naming is merely used to describe the technology in the embodiment of the present disclosure in detail, but the present invention is not limited in this regard. Therefore, combining the steps of said method into one step, dividing the steps into several steps, or rearranging the order of the steps is within the scope of the embodiment in the present disclosure.

In addition, the method 300, 400, 500 for checking a camera and a camera 100 applying the method of the embodiment of the present disclosure can adaptively adjust standards related to the problem of dust according to different apertures due to the fact that there are different standards related to the problem of dust when adopting different apertures. As a result, the operation of the camera 100 is more convenient.

It will be understood that the above description of embodiments is given by way of example only and that various modifications may be made by those with ordinary skill in the art. The above specification, examples and data provide a complete description of the structure and use of exemplary embodiments of the disclosure. Although various embodiments of the disclosure have been described above with a certain degree of particularity, or with reference to one or more individual embodiments, those with ordinary skill in the art could make numerous alterations to the disclosed embodiments without departing from the spirit or scope of this disclosure, and the scope thereof is determined by the claims that follow.

What is claimed is:

1. A method for checking a camera, comprising:
   capturing an image of an object using a photo-sensitive element;
   converting a color level value of each of a plurality of pixels of the image into an image gray level value;
   setting an aperture value;
   adjusting the predetermined gray level threshold value according to the aperture value; and displaying an alarm message on a screen of the camera when one of the image gray level values is higher than a predetermined gray level threshold value.

2. The method according to claim 1, further comprising:
detecting a position of one of the pixels in which the image gray level thereof is greater than the predetermined gray level threshold value, and displaying information of the position on the screen of the camera.

3. The method according to claim 1, wherein the step of capturing the image of the object using the photo-sensitive element comprises:
measuring a distance between the object and the photo-sensitive element; and
performing a focusing process and capturing the image of the object according to the distance.

4. A method for checking a camera, comprising:
capturing an image of an object using a photo-sensitive element;
acquiring a green level value of each of a plurality of pixels of the image;
setting an aperture value;
adjusting the predetermined green level threshold value according to the aperture value; and
displaying an alarm message on a screen of the camera when one of the green level values is higher than a predetermined green level threshold value.

5. The method according to claim 4, further comprising:
detecting a position of one of the pixels in which the green level value thereof is greater than the predetermined green level threshold value, and displaying information of the position on the screen of the camera.

6. The method according to claim 4, wherein the step of acquiring the green level value of each of the pixels of the image comprises:
obtaining a red level value, the green level value, and a blue level value of each of the pixels of the image,
wherein the step of displaying the alarm message on the screen of the camera when one of the green level values is greater than the predetermined green level threshold value comprises:
displaying the alarm message on the screen of the camera when one of the red, green, and blue level values is greater than a corresponding predetermined red level threshold value, the corresponding predetermined green level threshold value, or a corresponding predetermined blue level threshold value.

7. The method according to claim 4, wherein the step of capturing the image of the object using the photo-sensitive element comprises:
measuring a distance between the object and the photo-sensitive element; and
performing a focusing process and capturing the image of the object according to the distance.

* * * * *